United States Patent [19]

Ames

[11] Patent Number: 4,580,977
[45] Date of Patent: Apr. 8, 1986

[54] IDENTIFICATION METHOD AND APPARATUS

[76] Inventor: Sheryl L. Ames, 7300 NW. 10th Pl., Plantation, Fla. 33313

[21] Appl. No.: 695,382

[22] Filed: Jan. 28, 1985

[51] Int. Cl.$^4$ ............................................. A61C 19/04
[52] U.S. Cl. ...................................... 433/68; 433/229
[58] Field of Search ....................... 433/229, 70, 71, 68

[56] References Cited

U.S. PATENT DOCUMENTS

| | | | |
|---|---|---|---|
| 1,495,390 | 5/1924 | Hollingsworth | 433/71 |
| 2,183,624 | 12/1939 | Schwartz | 32/19 |
| 3,126,631 | 3/1964 | McCarthy et al. | 433/70 |
| 3,959,881 | 6/1976 | Kokal, Jr. | 32/19 |
| 4,324,547 | 4/1982 | Arcan et al. | 433/71 |
| 4,390,028 | 6/1983 | Okano et al. | 128/777 |
| 4,508,156 | 4/1985 | Banks et al. | 433/71 |

*Primary Examiner*—Robert Peshock
*Attorney, Agent, or Firm*—Richard M. Saccocio

[57] ABSTRACT

A method and apparatus for identification of persons using dental data is disclosed. A unique but simple bite wafer is inserted between the lower and upper jaws of a person and biting pressure is exerted on the wafer. The registrations made on the bite wafer are geometrically evaluated. The geometric data is permanently recorded for future use when identifications and/or comparisons are to be made. The recorded data is different for each person which enables the identification and comparisons.

16 Claims, 5 Drawing Figures

IDENTIFICATION METHOD AND APPARATUS

BACKGROUND OF THE INVENTION

1. Field of the Invention

This invention relates in general to the field of personnel identification and in particular to an inexpensive and easily performed method and apparatus for identifying and distinguishing both children and adults according to their bitemark configurations.

2. Description of the Prior Art

Identification and distinguishing persons of different age groups and within the different age groups has been a most desirable objective for many years. In the most common example, it is desired to determine or verify the identification of a particular person. That is, a live person is physically available to be tested or subjected to identification procedures and that person's identity is in question. The questioned identity may take the form of ascertaining that the person is a named or particular person. For example, verifying that the person is in fact "John Smith." Or, the questioned identification may take the form of determining the identification of a particular person whose identity is completely unknown. For example, determining the identification of the person whose physical presence is available but where there is little or no information available which suggests his or her identity.

In other more complicated cases of determining a person's identity, the person whose identity is in question is dead and may have been severely burned in a fire, or was dead a relatively long period of time, or other like situations where prior art identification characteristics are unavailable. And, for example, it is desired to know whether or not such a dead person is or is not a person who has been declared missing. Very often in this type of situation it is more important to verify that the dead person is not the person in question.

Regardless of which type of identification is being pursued, a minimum of two and perhaps three sets of identifying records are required. One of the person whose identity is questioned and the second for the person who is to be compared with the reference, the third being of record.

In the past, the primary and foremost method of identification of persons has been by the use of fingerprints. Fingerprint identification is, of course, based on the thought that no two people have the exact same fingerprints and that such fingerprints do not materially change with time. There is no question that throughout the years fingerprint identification procedures have been very successful. Many crimes have been solved through the use of fingerprints and the relatively sophisticated techniques utilized with fingerprint comparisons. Telltale fingerprints left at the scene of a crime have often been the single most important piece of evidence which was used to place the criminal at the scene of the crime and convict him at trial.

Notwithstanding the high success rate associated with fingerprint identification, such identification techniques and procedures do have their limitations and are relatively complicated. An expert technician must be used to record a person's fingerprints. Special ink, ink applicator and a special inking surface must be used by the expert technician in applying the ink to the person's fingers and then transferring the inked fingerprints onto heavy paper which then comprises the fingerprint record. When it is desired to make a comparison of fingerprints, the reference set of fingerprints must be photographically reproduced into a form such as a transparency which then allows the use of the special techniques used during comparison procedures. The expert must then make another set of fingerprints of the person whose identity is questioned; or, in other situations yet another expert must first dust for latent fingerprints left, for example, at the scene of a crime, and once found, must lift the latent prints by the use of special tape and place them onto a special card. Later, photographic reproductions of the latent set of fingerprints or the lifted latent fingerprints must be made and compared to the reference set of fingerprints. This is done by the expert who most painstakingly compares ridge for ridge, bifurcation for bifurcation, swirl for swirl, etc. If the fingerprints match, the bifurcations, number of ridges between distinguishing characteristics, swirls, and other unique characteristics will appear at the same location on each set of fingerprints. It is the expert who makes the comparison and who decides as to the identification. A lay person may not and cannot make these determinations and conclusions. Thus, experts are an essential and material part of the fingerprint identification process. In fact, without any one of such experts in any phase of the procedure, fingerprint identification would not be possible.

Costs are yet another disadvantage of identification of fingerprints. Inconvenience and lack of simplicity are still other factors which disfavor fingerprint identification. Yet, despite their limitations or disadvantages, fingerprint identification has been most useful. Probably because no other method or apparatus has been so well developed by long term use and improvements and prior to the present invention no other method and apparatus has been devised which is capable of matching the high degree of certainty of identifications made by fingerprints.

Where a reference or comparison set of fingerprints is not available or obtainable, such as in those examples earlier described, fingerprint identification is, of course, not a viable technique. This is a significant limitation.

Identification by use of teeth characteristics has in the past been attempted but has achieved only limited success. Such prior art techniques were based on the person's previous dental record. And, this technique has been used usually when the person to be identified is dead.

Since teeth do not materially change over the years and because teeth can survive fires, long term effects of water, time and other conditions which would deteriorate most body features, teeth have naturally lent themselves to attempts at identification. In such attempts, the subject's teeth are compared to the record of a person's teeth to determine if there are any similarities. Similarities may comprise missing teeth, capped teeth, teeth fillings, and the locations of such characteristics. This identification technique must necessarily rely on having a record of the person's dental history as well as first having a strong suspicion of the person's identity. Thus, such techniques have inherent limitations which do not permit widespread usage. These techniques tend only to supplement fingerprint identification methods and then are only marginally successful because of the need to originally suspect the person's identity and then find his dental records.

Accordingly, there is a need for new and useful identification procedures which are simple, convenient, inexpensive, easy to use, do not require numerous experts, and are effective.

Thus, an object of the present invention is to provide an identification method and apparatus which produces a record which can be conveniently and easily obtained by the individuals themselves or by other lay persons.

Another object of the present invention is to be able to produce an identification record at a minimal cost.

Another object of the present invention is to provide a method and apparatus which provides for personnel identification which is applicable to both children and adults and will be useful for an indeterminate and long number of years.

Another object of the present invention is to provide a method and apparatus for personnel identification which does not necessarily require an expert to make a comparison between a reference and a person whose identification may possibly match up with the reference.

Yet another object of the present invention is to provide a method and apparatus for personnel identification which has widespread use over a large population of individuals.

Another object of the present invention is to provide a method and apparatus for personnel identification which is reliable and possesses a high degree of certainty of the conclusions of comparison or non-comparison.

Another object of the present invention is to provide a method and apparatus for personnel identification which can readily be adaptable to computer usage including storage, recall, analysis of distinguishing characteristics, and rendering an opinion as to a positive or negative comparison.

Although not specifically mentioned, there are various other objects and advantages of the present invention which will be apparent to those ordinarily skilled in the art upon a fair reading and interpretation of the present specification, claims, and drawings, and which other objects are intended to be included within the present invention.

SUMMARY OF THE INVENTION

The above specifically-mentioned objects, as well as those not mentioned but implied, are achieved by the present invention which comprises a method and apparatus for identification of persons of all ages. The invention is premised upon the fact that the shape of each person's dental arches are unique for each particular individual.

A low cost but unique bite wafer is placed in the subject's mouth, who is then instructed to bite down on the wafer. The result is a bitemark registration for the teeth of the upper jaw and another one for the teeth of the lower jaw. Each bitemark registration is oriented relative to a square grid system having X and Y axes and in accordance with a procedure that causes each arch to be divided into two substantially equal halves. Two or more X and Y coordinates are measured on each arch half, with each set of X and Y coordinates corresponding to different but particular teeth. The measured data are then used to determine the slope of a line drawn between two teeth and on each arch half. The angle formed by intersection of the slope lines for each arch is also measured and recorded. The above data and calculated values are stored in an appropriate information storage and retrieval system for future use.

The reference bitemark registration may be updated as often as desired.

When an identification check is desired to be made, a bitemark registration is made of the person to be identified. The X and Y coordinates are determined and the slope of the lines and the intersecting angle of the slopes are then calculated as stated above. The data from the individual to be identified is then compared to the data contained in the information storage and retrieval system. The comparison can be used to indicate a positive or negative matchup with the prior recorded identification of a particular individual, or to attempt to determine the identity of the person to be identified by comparing his data with the data of the numerous individuals whose records are stored in the information system.

Various other objects, advantages, and features of the invention will become apparent to those skilled in the art from the following discussion taken in conjunction with the following drawings, in which:

DESCRIPTION OF THE PREFERRED EMBODIMENTS

Figure 1A:
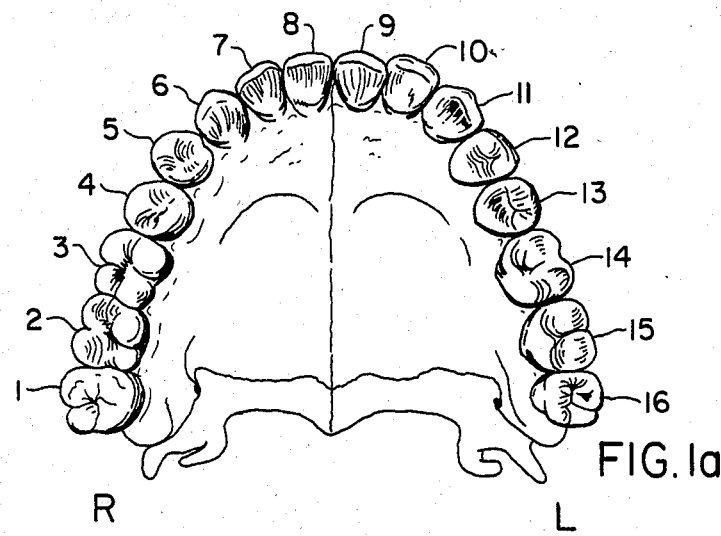
FIG. 1 is a plan view of the teeth of the lower and upper jaws of a person.

Reference is now made to the drawings where like characteristics are referred to among the various figures by the same reference numerals.

Figure 1B:
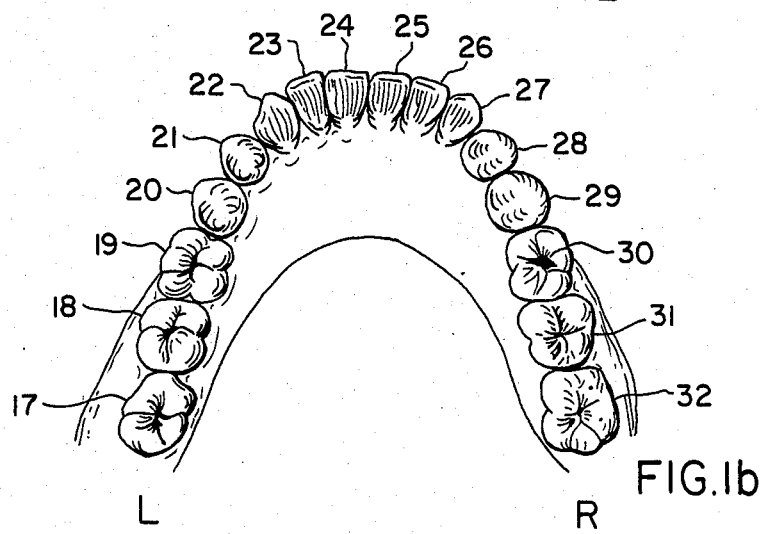

FIG. 1 illustrates all of the teeth of an adult person. FIG. 1 represents the upper jaw; FIG. 1b represents the lower jaw. The example shown in FIG. 1 represents an ideal situation, that is, no teeth are missing, not even the "21 year" molars. Moreover, FIG. 1 represents the permanent rather than the primary deciduous or baby teeth of a child. Teeth 1, 2, 3, 14, 15, 16, 17, 18, 19, 30, 31, and 32 are molars. The teeth numbered 1, 16, 17, and 32 are the "21 year" molars. Teeth 4, 5, 12, 13, 20, 21, 28, and 29 are premolars or bicuspids. Teeth 6, 11, 22, and 27 are canines or cuspids. Teeth 7, 8, 9; 10, 23, 24, 25, and 26 are incisors. The numerical system utilized in FIG. 1 is in accordance with the International Dentition Numbering System. The initials R & L refer to the right and left side of the jaw.

Figure 2:
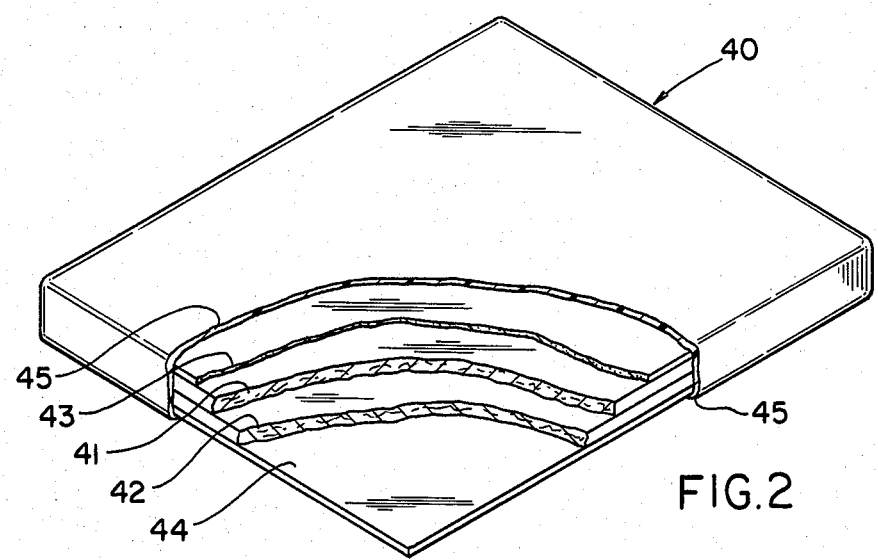
FIG. 2 is a schematic rendering of a bite wafer apparatus used in conjunction with the present invention.

FIG. 2 illustrates the inventive bite wafer 40. Two squares 41 and 42 of poster board cardboard approximately 2-2-½ inches on each side are interposed between two pieces of carbon paper 43 and 44. The carbon papers 43 and 44 are also cut in squares of substantially the same dimensions as cardboard squares 41 and 42. The lift-off surface of carbon papers 43 and 44 are arranged to be in surface contact with or facing cardboard squares 41 and 42. Carbon papers 43 and 44 are merely placed in contact with cardboard squares 41 and 42; that is, no adhesive or other like substance is used to secure carbon papers 43 and 44 to cardboard squares 41 and 42. A protective coating 45. which may be made from a transparent plastic film or other similar suitable material, is fitted over and around squares 41 and 42 and carbon pieces 43 and 44. It is preferable that protective covering 45 be substantially hermetically sealed around its edges to keep out moisture. In another embodiment, only one cardboard square is utilized within wafer 40. In this embodiment (not shown) the bitemark registration is made on both sides of the single cardboard square.

The size of the bite wafer 40 may be differently sized to accommodate children and adults and need not necessarily be square. It has been found that white poster board approximately 1/16-⅛ inch thick is most suitable for the cardboard pieces 41 and 42, which become the record of the bitemark, because of the ready transferability of the bitemark by carbon paper onto such cardboard, and because of the compressibility of this type of cardboard which allows the recording of the bitemark using only a relatively small amount of biting force. While poster board and the configuration of bite wafer 40 also allows the recording of the individual's name, date of impression, sex, date of birth, and any other information which may be pertinent, to be permanently recorded into the record by simply writing onto the bite wafer 40 through covering 45 by the use of a ball point pen, pencil, or any other semipointed device. This record should be made on both sides of the wafer 40 immediately before the registration is made to insure that no errors of recordation are made. Data showing right and left sides, upper or lower registrations, etc., should be prerecorded on the squares 41 and 42 to avoid possible errors. Once the bite wafer 40 is used, the pieces of carbon paper 43 and 44 are removed and discarded along with protective coating 45. The recorded bitemark registrations on squares 41 and 42 are kept together and processed as explained below.

Figures 3, 4:
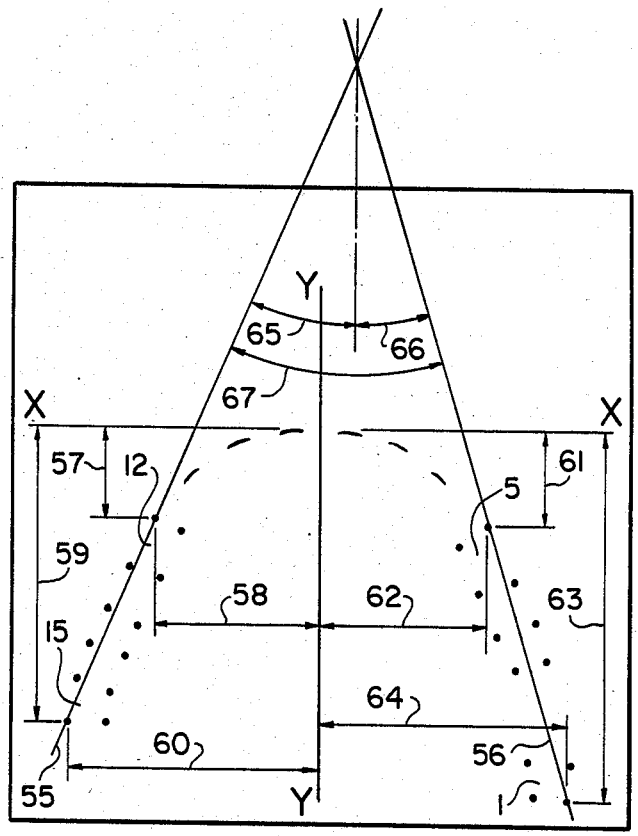
FIG. 3 is a schematic drawing of the bitemark registration made on one side of the wafer of FIG. 2 by the teeth of an individual to be recorded or identified; and, FIG. 4 is a schematic rendering of the registration made in FIG. 3 illustrating the measurements made and the calculated characteristics of the bitemark.

FIG. 3 illustrates a typical or representative record of an upper jaw bitemark registration made by a person having two missing teeth (numbers 2 and 16). The next to rear most right molar 2 is missing; molar numbered 16 is also missing. The cardboard piece 42 (not shown) would, of course, contain a record of the person's lower jaw. Items numbered 1, 3, 4, 5, 6, 7, 8, 9, 10, 11, 12, 13, 14 and 15 represent the registration left by upper teeth having the same numbers. The person's signature 46 can be signed by the individual whose teeth registration is on square 41 and may be used as an additional item of identity. The person's name 47, his date of birth 48, sex 49, and the date of the impression 50 are also recorded.

Once the bitemark registration is made, the registration characteristics are determined, then all the data is stored in an appropriate computer storage and retrieval system which may be readily accessible to any interested agency, police department, etc. The registration characteristics may then be used for subsequent identification procedures.

The identifying characteristics of a bitemark registration, such as that shown in FIG. 3, may be made as follows. FIG. 4 represents the same bitemark registration as shown in FIG. 3. The name and factual data of the individual are not shown in FIG. 4 for purposes of simplicity. In actual practice such data would, of course, be shown on card 41. Determination of the identifying characteristics as explained herein are made by a manual technique. The invention is not to be limited to a manual determination. Any machine-based or computer-based determination of the characteristics may also be used.

An X-Y set of axis is superimposed upon the bitemark registration. The X—X axis is caused to substantially coincide with the line passing through central incisors 8 and 9. The Y—Y axis is caused to bisect central incisors 8 and 9 so as to divide the bitemark registration into two substantially equal arch halves. The X—X axis is, of course, perpendicular to the Y—Y axis. The X—X axis and the Y—Y axis may in reality be located on a transparent film (not shown) which also contains a grid system and is placed over or on top of card 41. The grid coordinates or the distances from the X—X axis and the Y—Y axis are determined for two teeth on each arch half of the bitemark registration on card 41. It is preferred that the most spaced apart premolars (or bicuspids) and the molars be used for the identification characteristics. Thus, teeth pairs 5 and 1, 12 and 16, 21 and 17, and 28 and 32 should be used. If any of these teeth are missing, the molar (meaning either molar or premolar) adjacent to the missing tooth should be used in the pair. For example, if tooth 1 is missing, the 5 and 2 pair is used in place of the 5 and 1 pair. If both teeth 1 and 5 of the pair are missing, then teeth numbered 4 and 2 may be used. The fact that certain of the teeth are missing should be recorded. The missing teeth and their locations become additional items or characteristics of identification. The theoretical line between the most spaced apart molars (meaning molars and premolars) is capable of being more accurately located than the theoretical line between any two other teeth.

In FIG. 4, line 55 is a line drawn between teeth 12 and 15; line 56 is a line drawn between teeth 1 and 5. Line 55 accounts for missing tooth 16. The fact that tooth 2 is missing is not a factor in line 56 but is an additional identifying characteristic and should be recorded. Recording may be done on card 41 or other appropriate document which becomes part of the record.

The grid locations or X and Y dimensions are determined for each of teeth 1, 5, 12, and 15 at the indicated points of registration. Thus, dimensions or grid locations 57 and 58 are determined for tooth 12, 59 and 60 for tooth 15, 61 and 62 for tooth 5, and 63 and 64 for tooth 1. These dimensions or grid locations are not necessarily recorded. The slope of lines 55 and 56 may be determined by dividing the difference between the vertical dimensions for each tooth pair by the difference between the horizontal dimensions for the same tooth pair. For example, the slope of line 55 is distance 59 minus distance 57 divided by distance 60 minus distance 58; the slope of line 56 is distance 63 minus distance 61 divided by distance 64 minus distance 62. Each slope is recorded. By using the same dimensions, the angles 65 and 66 may be calculated (or measured from the card itself). Angle 65 is the angle between the Y—Y axis and line 55; angle 66 is the angle between the Y—Y axis and the line 56. Finally, angle 67 is calculated (angle 65 plus angle 66) or measured. All slopes and angles are recorded. The slopes and angles may be recorded directly on card 41.

For purposes of identification of a particular individual, only one slope and one included angle of one arch half is required. The additional slopes and angles increase the accuracy of the identification procedure as herein explained and described.

In order to determine the unknown identity of a person, it is necessary that that person's bitemark registration was previously made and the above bitemark characteristics determined. A bitemark registration is made of the person of questionable identification placing an unused wafer 40 in that person's mouth and applying appropriate biting forces. The characteristics that registration using the same registration points are then determined. The latter characteristics are subsequently input into a storage and retrieval system for purposes of attempting a matchup. If the sex and appropriate age of the person is known, that data may also be input into the system in order to narrow the scope of the matchup survey and reduce the overall time of the survey.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the breadth and scope of the claims here appended.

I claim as my invention:

1. Apparatus for making a bitemark registration of a person's upper or lower teeth comprising at least one wafer of a recording material capable of being slightly compressed by normal biting forces, one wafer of a transferring material capable of transferring said bitemark registration onto said recording material wafer, with said transferring material wafer being placed against one side of said recording material wafer.

2. The apparatus of claim 1, wherein said recording material wafer comprises cardboard.

3. The apparatus of claim 1, wherein said transferring material wafer comprises carbon paper.

4. The apparatus of claim 1, wherein said wafer of recording material and the said wafer of transferring material are sized and shaped to fit within a person's mouth.

5. The apparatus of claim 1, wherein said wafers are hermetically sealed by a plastic covering.

6. Apparatus for making a bitemark registration of a person's upper and lower teeth comprising two wafers of a recording material capable of being slightly compressed by normal biting forces, two wafers of a transferring material capable of transferring the registration of a person's teeth onto said recording material wafer, with one of said transferring material wafers being placed against one side of one of said recording material wafers and the other transferring material wafer being placed against one side of the other side of said recording material wafers, said recording material wafers being interposed between said transferring material wafers.

7. The apparatus of claim 1, wherein said recording material wafers comprise cardboard.

8. The apparatus of claim 6, wherein said transferring material wafers comprise carbon paper.

9. The apparatus of claim 6, wherein said wafer of recording material and said wafers of a transferring material are sized ad shaped to fit within a person's mouth.

10. The apparatus of claim 6, wherein said wafers are hermetically sealed by a plastic covering.

11. A method for establishing a record enabling the identification of persons comprising the steps of making a bitemark registration of one of a person's upper or lower teeth on bitemark registration apparatus;

for one of the lateral arch halves of said bitemark registration, determining the slope of the line connecting the two most spaced apart premolars and molars;

determining the angle between said line between the molars and the line substantially bisecting the bitemark registration into the two lateral arch halves; and, recording the slope and the angle.

12. The method of claim 1, including the steps of determining the slope and the angle between the line bisecting the lateral arch halves for the other lateral arch half and recording said slope and angle.

13. The method of claim 12, including the steps of determining the angle between the lines connecting the molars on each lateral arch half and recording said angle.

14. The method of claim 13, including the steps of making a registration of the other of said person's upper or lower teeth on bitemark registration apparatus, determining the slopes of the lines connecting the two most spaced apart premolars and molars, determining the angles between said slope lines and the line bisecting each lateral arch half of said other bitemark registration, determining the angle between the slope lines of said other bitemark registration, and recording said data.

15. The method of claim 1, including the steps of determining the location of a person's missing teeth and recording said locations.

16. The method of claim 1, including the steps of recording said person's date of birth, sex and name.

* * * * *